United States Patent
Kim

(10) Patent No.: US 11,708,615 B2
(45) Date of Patent: Jul. 25, 2023

(54) METHOD FOR DIAGNOSING LYMPHOMA VIA BACTERIAL METAGENOMIC ANALYSIS

(71) Applicant: MD HEALTHCARE INC., Seoul (KR)

(72) Inventor: Yoon-Keun Kim, Paju-si (KR)

(73) Assignee: MD HEALTHCARE INC., Seoul (KR)

( * ) Notice: Subject to any disclaimer, the term of this patent is extended or adjusted under 35 U.S.C. 154(b) by 0 days.

(21) Appl. No.: 16/757,231

(22) PCT Filed: Apr. 25, 2018

(86) PCT No.: PCT/KR2018/004798
§ 371 (c)(1),
(2) Date: Apr. 17, 2020

(87) PCT Pub. No.: WO2019/078432
PCT Pub. Date: Apr. 25, 2019

(65) Prior Publication Data
US 2020/0277656 A1    Sep. 3, 2020

(30) Foreign Application Priority Data

Oct. 18, 2017   (KR) .................. 10-2017-0135466
Apr. 24, 2018   (KR) .................. 10-2018-0047607

(51) Int. Cl.
C12Q 1/689    (2018.01)
C12Q 1/6886   (2018.01)

(52) U.S. Cl.
CPC .......... *C12Q 1/689* (2013.01); *C12Q 1/6886* (2013.01)

(58) Field of Classification Search
None
See application file for complete search history.

(56) References Cited

U.S. PATENT DOCUMENTS

| | | |
|---|---|---|
| 2008/0004208 A1 | 1/2008 | Seto et al. |
| 2011/0275073 A1 | 11/2011 | Gocke et al. |
| 2014/0086954 A1 | 3/2014 | Burcelin et al. |

FOREIGN PATENT DOCUMENTS

| | | | |
|---|---|---|---|
| CN | 106916889 A | 7/2017 | |
| EP | 2 484 752 A2 | 8/2012 | |
| EP | 2484752 A2 * | 8/2012 | ............ A61P 31/04 |
| JP | 2009-232743 A | 10/2009 | |
| JP | 2015-117220 A | 6/2015 | |
| JP | 2016-161480 A | 9/2016 | |
| KR | 10-2011-0025068 A | 3/2011 | |
| KR | 10-2011-0025603 A | 3/2011 | |
| KR | 10-2012-0121941 A | 11/2012 | |
| KR | 10-2016-0073157 A | 6/2016 | |
| WO | 2012/050513 A1 | 4/2012 | |
| WO | 2012/131099 A1 | 10/2012 | |
| WO | 2016/099076 A1 | 6/2016 | |
| WO | 2017/009693 A1 | 1/2017 | |
| WO | 2017009693 A1 | 1/2017 | |

OTHER PUBLICATIONS

Ferreri et al. (Journal of the National Cancer Institute 2006 vol. 98 p. 1375) (Year: 2006).*
The extended European Search Report dated Jun. 7, 2021, for corresponding EP Patent Application No. 18867803.1, 8 pages.
Jia et al., "Gut microbiota: a potential new territory for drug targeting", Nature Reviews: Drug Discovery, 2008, vol. 7, pp. 123-129.
Japanese Office Action for corresponding JP Application No. 2020-521551, dated Jun. 22, 2021, 14 pages.
Office Action dated Jan. 4, 2022 for corresponding Chinese Patent Application No. 201880067789.9.
Montassier et al., "Chemotherapy-driven dysbiosis in the intestinal microbiome", Alimentary Pharmacology and Therapeutics, 2015, vol. 42, pp. 515-528.
Yang et al., "Analysis of gut microbiota from patients with hematologic malignancy", China J Microecol, 2017, vol. 29, No. 10, pp. 1136-1139.
Yoo et al., "16S rRNA gene-based metagenomic analysis reveals differences in bacteria-derived extracellular vesicles in the urine of pregnant and non-pregnant women", Experimental & Molecular Medicine, 2016, vol. 48, pp. 1-8.

* cited by examiner

*Primary Examiner* — Katherine D Salmon
(74) *Attorney, Agent, or Firm* — Vorys, Sater, Seymour and Pease LLP; Mih Suhn Koh

(57) ABSTRACT

Provided is a method of diagnosing lymphoma by analyzing an increase or decrease in contents of specific bacterial extracellular vesicles by performing bacterial metagenomic analysis using normal individual and subject-derived samples, wherein a lymphoma risk group may be diagnosed and predicted early to delay the time of onset or prevent the onset of lymphoma with proper cure, and after onset, early diagnosis may be performed, thereby reducing the incidence of lymphoma and increasing a therapeutic effect.

2 Claims, 6 Drawing Sheets
Specification includes a Sequence Listing.

SEQUENCE LISTING

<160> NUMBER OF SEQ ID NOS: 2

<210> SEQ ID NO 1
<211> LENGTH: 50
<212> TYPE: DNA
<213> ORGANISM: Artificial Sequence

```
<220> FEATURE:
<223> OTHER INFORMATION: 16S_V3_F
<220> FEATURE:
<221> NAME/KEY: misc_feature
<222> LOCATION: (42)
<223> OTHER INFORMATION: a or g or c or t/u

<400> SEQUENCE: 1
tcgtcggcag cgtcagatgt gtataagaga cagcctacgg gnggcwgcag            50

<210> SEQ ID NO 2
<211> LENGTH: 55
<212> TYPE: DNA
<213> ORGANISM: Artificial Sequence
<220> FEATURE:
<223> OTHER INFORMATION: 16S_V4_R
<220> FEATURE:
<221> NAME/KEY: misc_feature
<222> LOCATION: (41)
<223> OTHER INFORMATION: a or c or t/u
<220> FEATURE:
<221> NAME/KEY: misc_feature
<222> LOCATION: (42)
<223> OTHER INFORMATION: a or g or c

<400> SEQUENCE: 2
gtctcgtggg ctcggagatg tgtataagag acaggactac hvgggtatct aatcc       55
```

METHOD FOR DIAGNOSING LYMPHOMA VIA BACTERIAL METAGENOMIC ANALYSIS

CROSS-REFERENCE TO RELATED APPLICATIONS

This application is a 371 of PCT/KR2018/004798, filed Apr. 25, 2018, which claims the benefit of priority from Korean Patent Application No. 10-2017-0135466, filed Oct. 18, 2017 and Korean Patent Application No. 10-2018-0047607, filed Apr. 24, 2018, the contents of each of which are incorporated herein by reference in its entirety.

SEQUENCE LISTING

The Sequence Listing submitted in text format (.txt) filed on Apr. 17, 2020, named "SequenceListing.txt", created on Mar. 27, 2020 (868 bytes), is incorporated herein by reference.

TECHNICAL FIELD

The present invention relates to a method for diagnosing lymphoma through a bacterial metagenomic analysis and, more specifically, to a method of diagnosing lymphoma, and the like by performing a bacterial metagenomic analysis using normal individual-derived and subject-derived samples to analyze an increase or decrease in the content of specific bacteria-derived extracellular vesicles.

BACKGROUND ART

Lymphoma is a group of blood cancers that originate from lymphocytes, mainly originating from the lymph nodes, but may develop in any lymph-related tissue. Typical symptoms include lymphadenopathy, night sweats, fever, weight loss, fatigue, etc. An enlarged lymph node is painless, and to this end, it is distinguished from lymph node swelling caused by infection. Basically, since lymphoma is blood cancer, surgical treatment may not generally work, but chemotherapy or radiation therapy is effective. According to data reported by the Korean Central Cancer Registry Center (KCCR) in 2011, in 2009, an average of 192,561 cancer cases occurred in Korea, and among them, an average annual occurrence of malignant lymphoma in men and women was 4,093 cases, which account for 2.13% of the overall cancer incidence. The average male and female numbers of the malignant lymphoma occurrence were 2,313 cases for men, and 1,780 cases for women. The incidence of lymphoma by age group including men and women was 22.1% in the 60 s, which is the highest, followed by 19.3% in the 50 s and 70 s and 15.4% in the 40 s.

As a risk factor of lymphoma, infection or abnormal immunoregulation is known as one of the causes of the development of lymphoma. HTLV-1 infection, lymphoma associated with the acquired immunodeficiency syndrome virus, chronic hepatitis C-associated lymphoma, Burkitt lymphoma associated with the EB virus, NK/T lymphoma, and lymphoma associated with *Helicobacter* bacteria are known to be associated with infections. In addition, lymphoma may develop even while immunity is reduced, and it is known that incidence increases in organ transplants, acquired immunodeficiency syndrome, congenital immunodeficiency syndrome, and autoimmune diseases. The diagnosis of lymphoma may be generally performed by lymph node biopsy, and when pathological tissue is obtained, basic staining and immunohistochemical staining are performed to distinguish types. Whether other organs are involved can be known by PET-CT.

Meanwhile, it is known that the number of microorganisms symbiotically living in the human body is 100 trillion which is 10 times the number of human cells, and the number of genes of microorganisms exceeds 100 times the number of human genes. A microbiota is a microbial community that includes bacteria, archaea, and eukaryotes present in a given habitat. The intestinal microbiota is known to play a vital role in human's physiological phenomena and significantly affect human health and diseases through interactions with human cells. Bacteria coexisting in human bodies secrete nanometer-sized vesicles to exchange information about genes, proteins, low molecular weight compound, and the like with other cells. The mucous membranes form a physical barrier membrane that does not allow particles with the size of 200 nm or more to pass therethrough, and thus bacteria symbiotically living in the mucous membranes are unable to pass therethrough, but bacteria-derived extracellular vesicles have a size of approximately 100 nm or less and thus relatively freely pass through the mucous membranes and are absorbed into the human body.

Metagenomics, also called environmental genomics, may be analytics for metagenomic data obtained from samples collected from the environment (Korean Patent Publication No. 2011-073049). Recently, the bacterial composition of human microbiota has been listed using a method based on 16s ribosomal RNA (16s rRNA) base sequences, and 16s rDNA base sequences, which are genes of 16s ribosomal RNA, are analyzed using a next generation sequencing (NGS) platform. However, for the onset of lymphoma, a method of identifying a causative factor of lymphoma through metagenomic analysis of bacterial vesicles in a human-derived material such as blood or urine to predict or diagnose lymphoma has not been reported yet.

DISCLOSURE

Technical Problem

The present inventors extracted genes from bacteria-derived extracellular vesicles present in blood as normal individual-derived and subject-derived samples and performed a metagenomic analysis in this regard in order to diagnose the causal factors and risk of lymphoma in advance, and as a result, identified bacteria-derived extracellular vesicles which may act as a causal factor of lymphoma, thereby completing the present invention based on this.

Therefore, an object of the present invention is to provide a method of providing information for diagnosing lymphoma, a method of diagnosing lymphoma, a method of predicting the risk of lymphoma onset, and the like through the metagenomic analysis of bacteria-derived extracellular vesicles.

However, the technical goals of the present invention are not limited to the aforementioned goals, and other unmentioned technical goals will be clearly understood by those of ordinary skill in the art from the following description.

Technical Solution

To achieve the above-described object of the present invention, there is provided a method of providing information for lymphoma diagnosis, comprising the following processes:

(a) extracting DNAs from extracellular vesicles isolated from normal individual and subject samples;

(b) performing polymerase chain reaction (PCR) on the extracted DNA using a pair of primers comprising SEQ ID NO: 1 and SEQ ID NO: 2; and (c) comparing an increase or decrease in content of bacteria-derived extracellular vesicles of the subject-derived sample with that of a normal individual-derived sample through sequencing of a product of the PCR.

The present invention also provides a method of diagnosing lymphoma, comprising the following processes:

(a) extracting DNAs from extracellular vesicles isolated from normal individual and subject samples;

(b) performing polymerase chain reaction (PCR) on the extracted DNA using a pair of primers comprising SEQ ID NO: 1 and SEQ ID NO: 2; and (c) comparing an increase or decrease in content of bacteria-derived extracellular vesicles of the subject-derived sample with that of a normal individual-derived sample through sequencing of a product of the PCR.

The present invention also provides a method of predicting a risk for lymphoma, comprising the following processes:

(a) extracting DNAs from extracellular vesicles isolated from normal individual and subject samples;

(b) performing polymerase chain reaction (PCR) on the extracted DNA using a pair of primers comprising SEQ ID NO: 1 and SEQ ID NO: 2; and (c) comparing an increase or decrease in content of bacteria-derived extracellular vesicles of the subject-derived sample with that of a normal individual-derived sample through sequencing of a product of the PCR.

In one embodiment of the present invention, in process (c), the lymphoma may be diagnosed by comparing an increase or decrease in content of extracellular vesicles derived from one or more bacteria selected from the group consisting of the phylum Cyanobacteria, the phylum Thermi, and the phylum Euryarchaeota.

In one embodiment of the present invention, the normal individual and subject samples may be blood.

In another embodiment of the present invention, in process (c), the lymphoma may be diagnosed by comparing an increase or decrease in content of extracellular vesicles derived from one or more bacteria selected from the group consisting of the class Deinococci, the class Chloroplast, and the class Betaproteobacteria.

In another embodiment of the present invention, in process (c), the lymphoma may be diagnosed by comparing an increase or decrease in content of extracellular vesicles derived from one or more bacteria selected from the group consisting of the order Deinococcales, the order Rickettsiales, the order Streptophyta, the order Rhizobiales, the order Oceanospirillales, the order Pasteurellales, and the order Neisseriales.

In another embodiment of the present invention, in process (c), the lymphoma may be diagnosed by comparing an increase or decrease in content of extracellular vesicles derived from one or more bacteria selected from the group consisting of the family Erythrobacteraceae, the family Rhodospirillaceae, the family Deinococcaceae, the family Nocardioidaceae, the family Oxalobacteraceae, the family mitochondria, the family Lactobacillaceae, the family Ruminococcaceae, the family Halomonadaceae, the family Micrococcaceae, the family Corynebacteriaceae, the family Propionibacteriaceae, the family Prevotellaceae, the family Burkholderiaceae, the family Actinomycetaceae, the family Tissierellaceae, the family Pasteurellaceae, the family Carnobacteriaceae, the family Neisseriaceae, and the family Alcanivoracaceae.

In another embodiment of the present invention, in process (c), the lymphoma may be diagnosed by comparing an increase or decrease in content of extracellular vesicles derived from one or more bacteria selected from the group consisting of the genus *Cupriavidus*, the genus *Deinococcus*, the genus *Clostridium*, the genus *Dialister*, the genus *Faecalibacterium*, the genus *Lactobacillus*, the genus *Citrobacter*, the genus *Micrococcus*, the genus *Corynebacterium*, the genus *Propionibacterium*, the genus *Anaerococcus*, the genus *Porphyromonas*, the genus *Prevotella*, the genus *Veillonella*, the genus *Rothia*, the genus *Actinomyces*, the genus *Haemophilus*, the genus *Peptomphilus*, the genus *Capnocytophaga*, the genus *Lautropia*, the genus *Granulicatella*, the genus *Finegoldia*, the genus *Neisseria*, the genus *Selenomonas*, and the genus *Alcanivorax*.

In another embodiment of the present invention, process (c) may comprise comparing an increase or decrease in content of extracellular vesicles derived from one or more bacteria selected from the group consisting of the phylum Cyanobacteria, the phylum Thermi, and the phylum Euryarchaeota;

extracellular vesicles derived from one or more bacteria selected from the group consisting of the class Deinococci, the class Chloroplast, and the class Betaproteobacteria;

extracellular vesicles derived from one or more bacteria selected from the group consisting of the order Deinococcales, the order Rickettsiales, the order Streptophyta, the order Rhizobiales, the order Oceanospirillales, the order Pasteurellales, and the order Neisseriales;

extracellular vesicles derived from one or more bacteria selected from the group consisting of the family Erythrobacteraceae, the family Rhodospirillaceae, the family Deinococcaceae, the family Nocardioidaceae, the family Oxalobacteraceae, the family mitochondria, the family Lactobacillaceae, the family Ruminococcaceae, the family Halomonadaceae, the family Micrococcaceae, the family Corynebacteriaceae, the family Propionibacteriaceae, the family Prevotellaceae, the family Burkholderiaceae, the family Actinomycetaceae, the family Tissierellaceae, the family Pasteurellaceae, the family Carnobacteriaceae, the family Neisseriaceae, and the family Alcanivoracaceae; or extracellular vesicles derived from one or more bacteria selected from the group consisting of the genus *Cupriavidus*, the genus *Deinococcus*, the genus *Clostridium*, the genus *Dialister*, the genus *Faecalibacterium*, the genus *Lactobacillus*, the genus *Citrobacter*, the genus *Micrococcus*, the genus *Corynebacterium*, the genus *Propionibacterium*, the genus *Anaerococcus*, the genus *Porphyromonas*, the genus *Prevotella*, the genus *Veillonella*, the genus *Rothia*, the genus *Actinomyces*, the genus *Haemophilus*, the genus *Peptoniphilus*, the genus *Capnocytophaga*, the genus *Lautropia*, the genus *Granulicatella*, the genus *Finegoldia*, the genus *Neisseria*, the genus *Selenomonas*, and the genus *Alcanivorax*.

In another embodiment of the present invention, in process (c), in comparison with the normal individual-derived sample, it is possible to diagnose an increase in the content of the following as lymphoma:

extracellular vesicles derived from bacteria of the class Betaproteobacteria, extracellular vesicles derived from one or more bacteria selected from the group consisting of the order Oceanospirillales, the order Pasteurellales, and the order Neisseriales, extracellular vesicles derived from one or more bacteria selected from the group consisting of the family Micrococcaceae, the family Corynebacteriaceae, the family Propionibacteriaceae, the family Prevotellaceae, the family Burkholderiaceae, the family Actinomycetaceae, the family Tissierellaceae, the family Pasteurellaceae, the family Carnobacteriaceae, the family Neisseriaceae, and the family Alcanivoracaceae, or extracellular vesicles derived from one or more bacteria selected from the group consisting of the genus *Micrococcus*, the genus *Corynebacterium*, the genus *Propionibacterium*, the genus *Anaerococcus*, the genus *Porphyromonas*, the genus *Prevotella*, the genus *Veillonella*, the genus *Rothia*, the genus *Actinomyces*, the genus *Haemophilus*, the genus *Peptoniphilus*, the genus *Capnocytophaga*, the genus *Lautropia*, the genus *Granulicatella*, the genus *Finegoldia*, the genus *Neisseria*, the genus *Selenomonas*, and the genus *Alcanivorax*.

In another embodiment of the present invention, in process (c), in comparison with the normal individual-derived sample, it is possible to diagnose a decrease in the content of the following as lymphoma:

extracellular vesicles derived from one or more bacteria selected from the group consisting of the phylum Cyanobacteria, the phylum Thermi, and the phylum Euryarchaeota, extracellular vesicles derived from one or more bacteria selected from the group consisting of the class Deinococci, and the class Chloroplast, extracellular vesicles derived from one or more bacteria selected from the group consisting of the order Deinococcales, the order Rickettsiales, the order Streptophyta, and the order Rhizobiales, extracellular vesicles derived from one or more bacteria selected from the group consisting of the family Erythrobacteraceae, the family Rhodospirillaceae, the family Deinococcaceae, the family Nocardioidaceae, the family Oxalobacteraceae, the family mitochondria, the family Lactobacillaceae, the family Ruminococcaceae, and the family Halomonadaceae, or extracellular vesicles derived from one or more bacteria selected from the group consisting of the genus *Cupriavidus*, the genus *Deinococcus*, the genus *Clostridium*, the genus *Dialister*, the genus *Faecalibacterium*, the genus *Lactobacillus*, and the genus *Citrobacter*.

In another embodiment of the present invention, the blood may be whole blood, serum, plasma, or blood mononuclear cells.

Advantageous Effects

Extracellular vesicles secreted from bacteria present in the environment can be absorbed into the body and have a direct influence on the development of cancer, and since it is difficult to enable early diagnosis of lymphoma before symptoms are shown, effective treatment is difficult. Therefore, lymphoma risk groups can be diagnosed and predicted early by previously diagnosing a causative factor and the risk of the onset of lymphoma through the metagenomic analysis of bacterial extracellular vesicles using a human-derived sample according to the present invention, and the time of onset can be delayed or the onset of the disease can be prevented with proper care. In addition, since lymphoma can be diagnosed early after onset, the incidence of lymphoma can be reduced and a therapeutic effect can increase, and the progress of the disease can be improved or the recurrence of the disease can be prevented by identifying causative factors through the metagenomic analysis on patients diagnosed with lymphoma to avoid exposure to the relevant factors.

BEST MODE

Figure 1A:
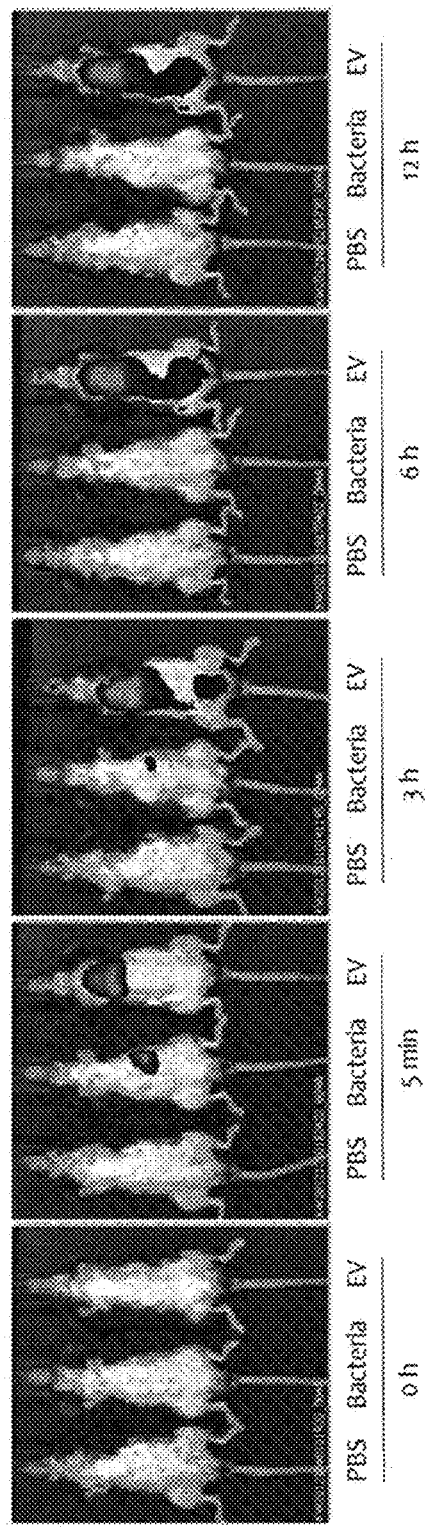
FIG. 1A illustrates images showing the distribution pattern of bacteria and extracellular vesicles over time after intestinal bacteria and bacteria-derived extracellular vesicles (EVs) were orally administered to mice.

The present invention relates to a method of diagnosing lymphoma through bacterial metagenomic analysis. The inventors of the present invention extracted genes from bacteria-derived extracellular vesicles using a normal individual and a subject-derived sample, performed metagenomic analysis thereon, and identified bacteria-derived extracellular vesicles capable of acting as a causative factor of lymphoma.

Therefore, the present invention provides a method of providing information for diagnosing lymphoma, the method comprising:

(a) extracting DNAs from extracellular vesicles isolated from normal individual and subject samples;

(b) performing polymerase chain reaction (PCR) on the extracted DNA using a pair of primers comprising SEQ ID NO: 1 and SEQ ID NO: 2; and (c) comparing an increase or decrease in content of bacteria-derived extracellular vesicles of the subject-derived sample with that of a normal individual-derived sample through sequencing of a product of the PCR.

The term "lymphoma diagnosis" as used herein refers to determining whether a patient has a risk for lymphoma, whether the risk for lymphoma is relatively high, or whether lymphoma has already occurred. The method of the present invention may be used to delay the onset of lymphoma through special and appropriate care for a specific patient, which is a patient having a high risk for lymphoma or prevent the onset of lymphoma. In addition, the method may be clinically used to determine treatment by selecting the most appropriate treatment method through early diagnosis of lymphoma.

The term "metagenome" as used herein refers to the total of genomes including all viruses, bacteria, fungi, and the like in isolated regions such as soil, the intestines of animals, and the like, and is mainly used as a concept of genomes that explains identification of many microorganisms at once using a sequencer to analyze non-cultured microorganisms. In particular, a metagenome does not refer to a genome of one species, but refers to a mixture of genomes, including genomes of all species of an environmental unit. This term originates from the view that, when defining one species in a process in which biology is advanced into omics, various species as well as existing one species functionally interact with each other to form a complete species. Technically, it is the subject of techniques that analyzes all DNAs and RNAs regardless of species using rapid sequencing to identify all species in one environment and verify interactions and metabolism. In the present invention, bacterial metagenomic analysis is performed using bacteria-derived extracellular vesicles isolated from, for example, blood.

In the present invention, the normal individual and subject sample may be blood or urine, and the blood may be preferably whole blood, serum, plasma, or blood mononuclear cells, but the present invention is not limited thereto.

In an embodiment of the present invention, metagenomic analysis is performed on the bacteria-derived extracellular vesicles, and bacteria-derived extracellular vesicles capable of acting as a cause of the onset of lymphoma were actually identified by analysis at phylum, class, order, family, and genus levels.

More particularly, in one embodiment of the present invention, as a result of performing bacterial metagenomic analysis on extracellular vesicles present in subject-derived blood samples at a phylum level, the content of extracellular vesicles derived from bacteria belonging to the phylum Cyanobacteria, the phylum Thermi, and the phylum Euryarchaeota was significantly different between lymphoma patients and normal individuals (see Example 4).

More particularly, in one embodiment of the present invention, as a result of performing bacterial metagenomic analysis on extracellular vesicles present in subject-derived blood samples at a class level, the content of extracellular vesicles derived from bacteria belonging to the class Deinococci, the class Chloroplast, and the class Betaproteobacteria was significantly different between lymphoma patients and normal individuals (see Example 4).

More particularly, in one embodiment of the present invention, as a result of performing bacterial metagenomic analysis on extracellular vesicles present in subject-derived blood samples at an order level, the content of extracellular vesicles derived from bacteria belonging to the order Deinococcales, the order Rickettsiales, the order Streptophyta, the order Rhizobiales, the order Oceanospirillales, the order Pasteurellales, and the order Neisseriales was significantly different between lymphoma patients and normal individuals (see Example 4).

More particularly, in one embodiment of the present invention, as a result of performing bacterial metagenomic analysis on extracellular vesicles present in subject-derived blood samples at a family level, the content of extracellular vesicles derived from bacteria belonging to the family Erythrobacteraceae, the family Rhodospirillaceae, the family Deinococcaceae, the family Nocardioidaceae, the family Oxalobacteraceae, the family mitochondria, the family Lactobacillaceae, the family Ruminococcaceae, the family Halomonadaceae, the family Micrococcaceae, the family Corynebacteriaceae, the family Propionibacteriaceae, the family Prevotellaceae, the family Burkholderiaceae, the family Actinomycetaceae, the family Tissierellaceae, the family Pasteurellaceae, the family Carnobacteriaceae, the family Neisseriaceae, and the family Alcanivoracaceae was significantly different between lymphoma patients and normal individuals (see Example 4).

More particularly, in one embodiment of the present invention, as a result of performing bacterial metagenomic analysis on extracellular vesicles present in subject-derived blood samples at a genus level, the content of extracellular vesicles derived from bacteria belonging to the genus *Cupriavidus*, the genus *Deinococcus*, the genus *Clostridium*, the genus *Dialister*, the genus *Faecalibacterium*, the genus *Lactobacillus*, the genus *Citrobacter*, the genus *Micrococcus*, the genus *Corynebacterium*, the genus *Propionibacterium*, the genus *Anaerococcus*, the genus *Porphyromonas*, the genus *Prevotella*, the genus *Veillonella*, the genus *Rothia*, the genus *Actinomyces*, the genus *Haemophilus*, the genus *Peptoniphilus*, the genus *Capnocytophaga*, the genus *Lautropia*, the genus *Granulicatella*, the genus *Finegoldia*, the genus *Neisseria*, the genus *Selenomonas*, and the genus *Alcanivorax* was significantly different between lymphoma patients and normal individuals (see Example 4).

Through the results of the examples, it was confirmed that distribution variables of the identified bacteria-derived extracellular vesicles could be usefully used for the prediction of the onset of lymphoma.

MODE OF THE INVENTION

Hereinafter, the present invention will be described with reference to exemplary examples to aid in understanding of the present invention. However, these examples are provided only for illustrative purposes and are not intended to limit the scope of the present invention.

EXAMPLES

Example 1. Analysis of In Vivo Absorption, Distribution, and Excretion Patterns of Intestinal Bacteria and Bacteria-Derived Extracellular Vesicles To evaluate whether intestinal bacteria and bacteria-derived extracellular vesicles are systematically absorbed through the gastrointestinal tract, an experiment was conducted using the following method. More particularly, 50 μg of each of intestinal bacteria and the bacteria-derived extracellular vesicles (EVs), labeled with fluorescence, were orally administered to the gastrointestinal tracts of mice, and fluorescence was measured at 0 h, and after 5 min, 3 h, 6 h, and 12 h. As a result of observing the entire images of mice, as illustrated in FIG. 1A, the bacteria were not systematically absorbed when administered, while the bacteria-derived EVs were systematically absorbed at 5 min after administration, and, at 3 h after administration, fluorescence was strongly observed in the bladder, from which it was confirmed that the EVs were excreted via the urinary system, and were present in the bodies up to 12 h after administration.

Figure 1B:
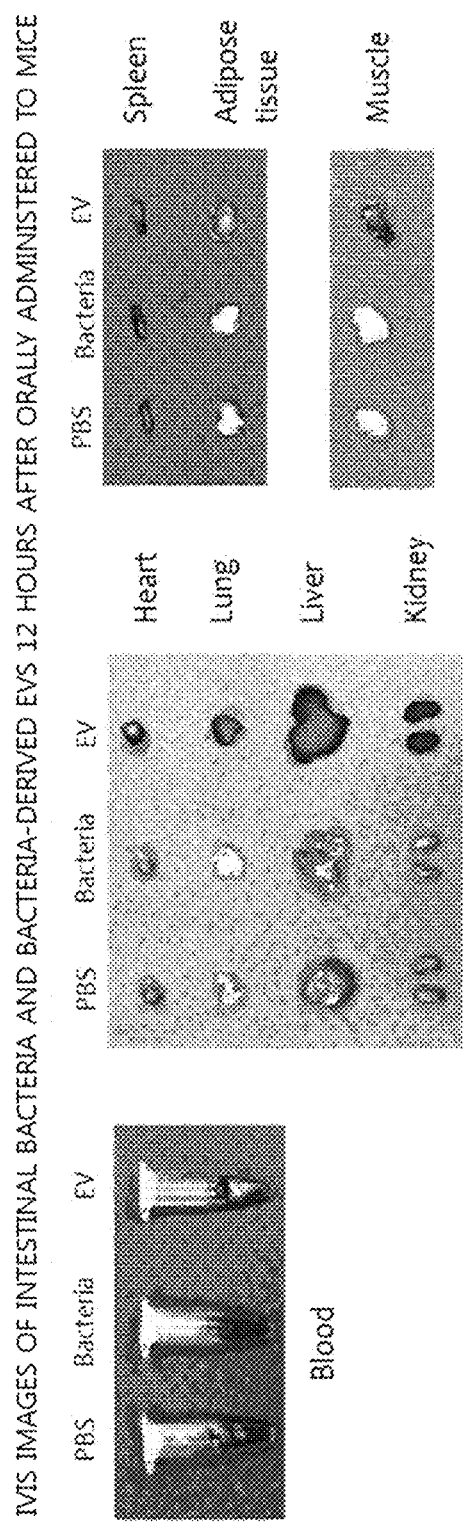
FIG. 1B illustrates images showing the distribution pattern of bacteria and EVs after being orally administered to mice and, at 12 hours, blood and various organs were extracted.

After intestinal bacteria and intestinal bacteria-derived extracellular vesicles were systematically absorbed, to evaluate a pattern of invasion of intestinal bacteria and the bacteria-derived EVs into various organs in the human body after being systematically absorbed, 50 μg of each of the bacteria and bacteria-derived EVs, labeled with fluorescence, were administered using the same method as that used above, and then, at 12 h after administration, blood, the heart, the lungs, the liver, the kidneys, the spleen, adipose tissue, and muscle were extracted from each mouse. As a result of observing fluorescence in the extracted tissues, as illustrated in FIG. 1B, it was confirmed that the intestinal bacteria were not absorbed into each organ, while the bacteria-derived EVs were distributed in the blood, heart, lungs, liver, kidneys, spleen, adipose tissue, and muscle.

Example 2. Vesicle Isolation and DNA Extraction from Blood

To isolate extracellular vesicles and extract DNA, from blood, first, blood was added to a 10 ml tube and centrifuged at 3,500×g and 4° C. for 10 min to precipitate a suspension, and only a supernatant was collected, which was then placed in a new 10 ml tube. The collected supernatant was filtered using a 0.22 μm filter to remove bacteria and impurities, and then placed in centrifugal filters (50 kD) and centrifuged at 1500×g and 4° C. for 15 min to discard materials with a smaller size than 50 kD, and then concentrated to 10 ml. Once again, bacteria and impurities were removed therefrom using a 0.22 μm filter, and then the resulting concentrate was subjected to ultra-high speed centrifugation at 150,000×g and 4° C. for 3 hours by using a Type 90ti rotor to remove a supernatant, and the agglomerated pellet was dissolved with phosphate-buffered saline (PBS), thereby obtaining vesicles.

100 μl of the extracellular vesicles isolated from the blood according to the above-described method was boiled at 100° C. to allow the internal DNA to come out of the lipid and then cooled on ice. Next, the resulting vesicles were centrifuged at 10,000×g and 4° C. for 30 minutes to remove the remaining suspension, only the supernatant was collected, and then the amount of DNA extracted was quantified using a NanoDrop sprectrophotometer. In addition, to verify whether bacteria-derived DNA was present in the extracted DNA, PCR was performed using 16s rDNA primers shown in Table 1 below.

TABLE 1

| Primer | | Sequence | SEQ ID NO. |
|---|---|---|---|
| 16S rDNA | 16S_V3_F | 5'-TCGTCGGCAGCGTC AGATGTGTATAAGAG | 1 |

TABLE 1-continued

| Primer | | Sequence | SEQ ID NO. |
|---|---|---|---|
| | | ACAGCCTACGGGNGG CWGCAG-3' | |
| | 16S_V4_R | 5'-GTCTCGTGGGCTCG GAGATGTGTATAAGA GACAGGACTACHVGG GTATCTAATCC-3' | 2 |

Example 3. Metagenomic Analysis Using DNA Extracted from Blood

DNA was extracted using the same method as that used in Example 2, and then PCR was performed thereon using 16S rDNA primers shown in Table 1 to amplify DNA, followed by sequencing (Illumina MiSeq sequencer). The results were output as standard flowgram format (SFF) files, and the SFF files were converted into sequence files (.fasta) and nucleotide quality score files using GS FLX software (v2.9), and then credit rating for reads was identified, and portions with a window (20 bps) average base call accuracy of less than 99% (Phred score<20) were removed. After removing the low-quality portions, only reads having a length of 300 bps or more were used (Sickle version 1.33), and, for operational taxonomy unit (OTU) analysis, clustering was performed using UCLUST and USEARCH according to sequence similarity. In particular, clustering was performed based on sequence similarity values of 94% for genus, 90% for family, 85% for order, 80% for class, and 75% for phylum, and phylum, class, order, family, and genus levels of each OTU were classified, and bacteria with a sequence similarity of 97% or more were analyzed (QIIME) using 16S DNA sequence databases (108,453 sequences) of BLASTN and GreenGenes.

Example 4. Lymphoma Diagnostic Model Based on Metagenomic Analysis of Bacteria-Derived EVs Isolated from Blood EVs were isolated from blood samples of 63 lymphoma patients and 53 normal individuals, the two groups matched in age and gender, and then metagenomic sequencing was performed thereon using the method of Example 3. For the development of a diagnostic model, first, a strain exhibiting a p value of less than 0.05 between two groups in a t-test and a difference of two-fold or more between two groups was selected, and then an area under curve (AUC), sensitivity, and specificity, which are diagnostic performance indexes, were calculated by logistic regression analysis.

Figure 2:
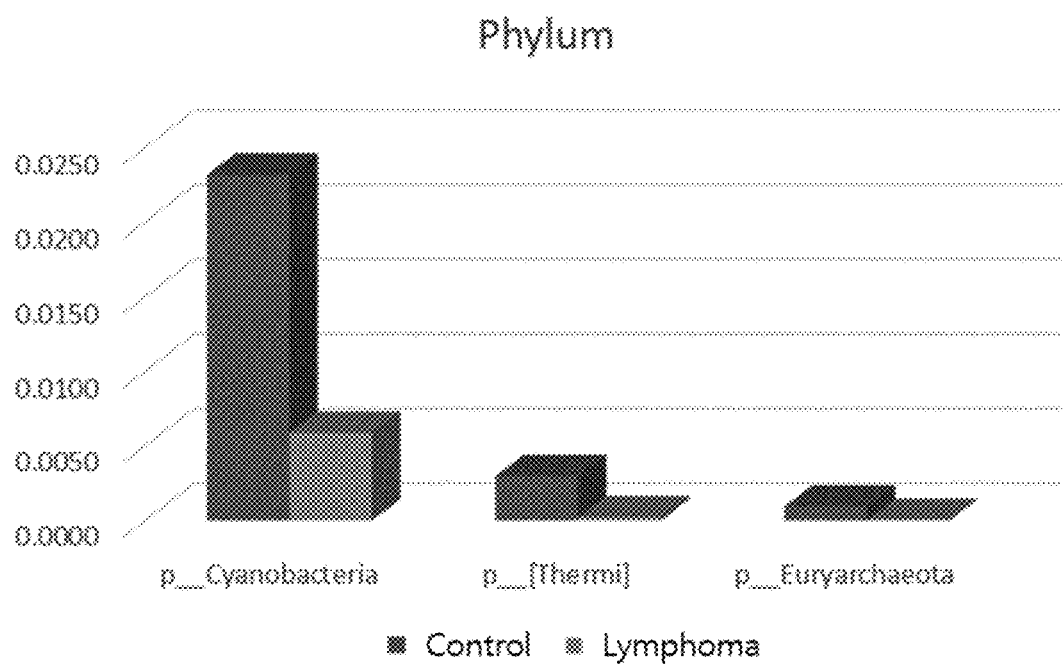
FIG. 2 is a result showing the distribution of bacteria-derived extracellular vesicles (EVs), which is significant in diagnostic performance at the phylum level by isolating bacteria-derived vesicles from blood of a patient with lymphoma and a normal individual, and then performing a metagenomic analysis.

As a result of analyzing bacteria-derived EVs in blood at a phylum level, a diagnostic model developed using bacteria belonging to the phylum Cyanobacteria, the phylum Thermi, and the phylum Euryarchaeota as a biomarker exhibited significant diagnostic performance for lymphoma (see Table 2 and FIG. 2).

TABLE 2

| | Control | | Lymphoma | | t-test | | | | | |
|---|---|---|---|---|---|---|---|---|---|---|
| Taxon | Mean | SD | Mean | SD | p-value | Ratio | AUC | Accuracy | sensitivity | specificity |
| p__Cyanobacteria | 0.0232 | 0.0369 | 0.0059 | 0.0142 | 0.0022 | 0.25 | 0.74 | 0.66 | 0.40 | 0.87 |
| p__[Thermi] | 0.0030 | 0.0059 | 0.0002 | 0.0008 | 0.0016 | 0.08 | 0.71 | 0.66 | 0.34 | 0.94 |
| p__Euryarchaeota | 0.0009 | 0.0022 | 0.0000 | 0.0002 | 0.0039 | 0.03 | 0.63 | 0.63 | 0.21 | 0.98 |

Figure 3:
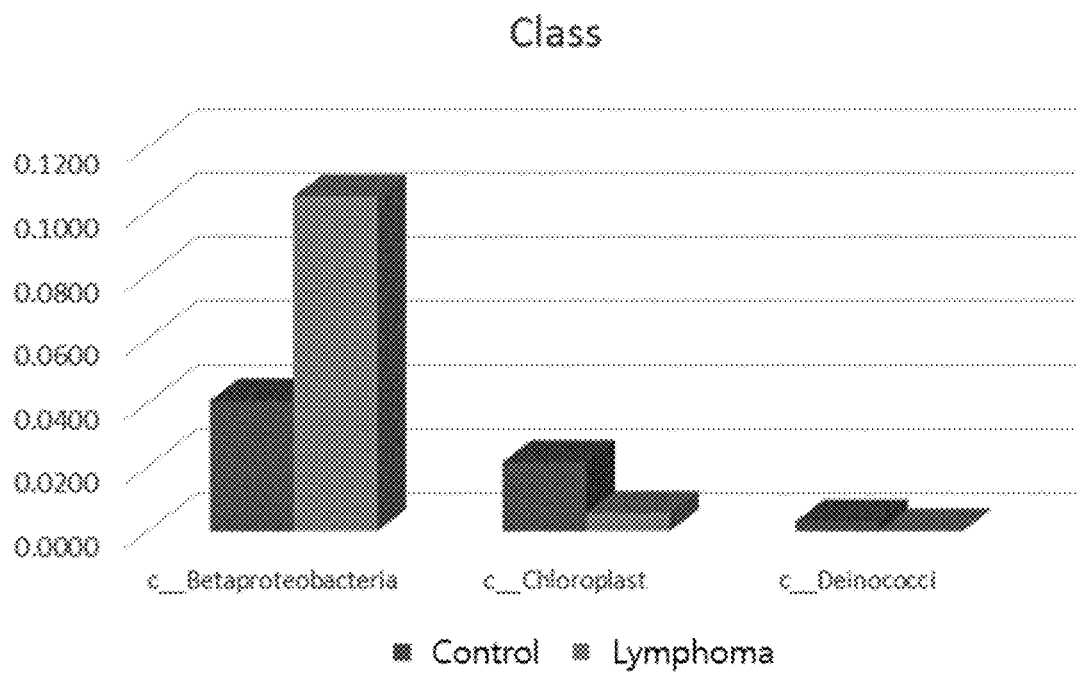
FIG. 3 is a result showing the distribution of bacteria-derived extracellular vesicles (EVs), which is significant in diagnostic performance at the class level by isolating bacteria-derived vesicles from blood of a patient with lymphoma and a normal individual, and then performing a metagenomic analysis.

As a result of analyzing bacteria-derived EVs in blood at a phylum level, a diagnostic model developed using bacteria belonging to the class Deinococci, the class Chloroplast, and the class Betaproteobacteria as a biomarker exhibited significant diagnostic performance for lymphoma (see Table 3 and FIG. 3).

TABLE 3

| Taxon | Control | | Lymphoma | | t-test | | | | | |
|---|---|---|---|---|---|---|---|---|---|---|
| | Mean | SD | Mean | SD | p-value | Ratio | AUC | Accuracy | sensitivity | specificity |
| c__Deinococci | 0.0030 | 0.0059 | 0.0002 | 0.0008 | 0.0016 | 0.08 | 0.71 | 0.66 | 0.34 | 0.94 |
| c__Chloroplast | 0.0216 | 0.0365 | 0.0057 | 0.0142 | 0.0043 | 0.26 | 0.71 | 0.67 | 0.40 | 0.90 |
| c__Betaproteobacteria | 0.0408 | 0.0440 | 0.1045 | 0.0486 | 0.0000 | 2.56 | 0.91 | 0.88 | 0.87 | 0.89 |

Figure 4:
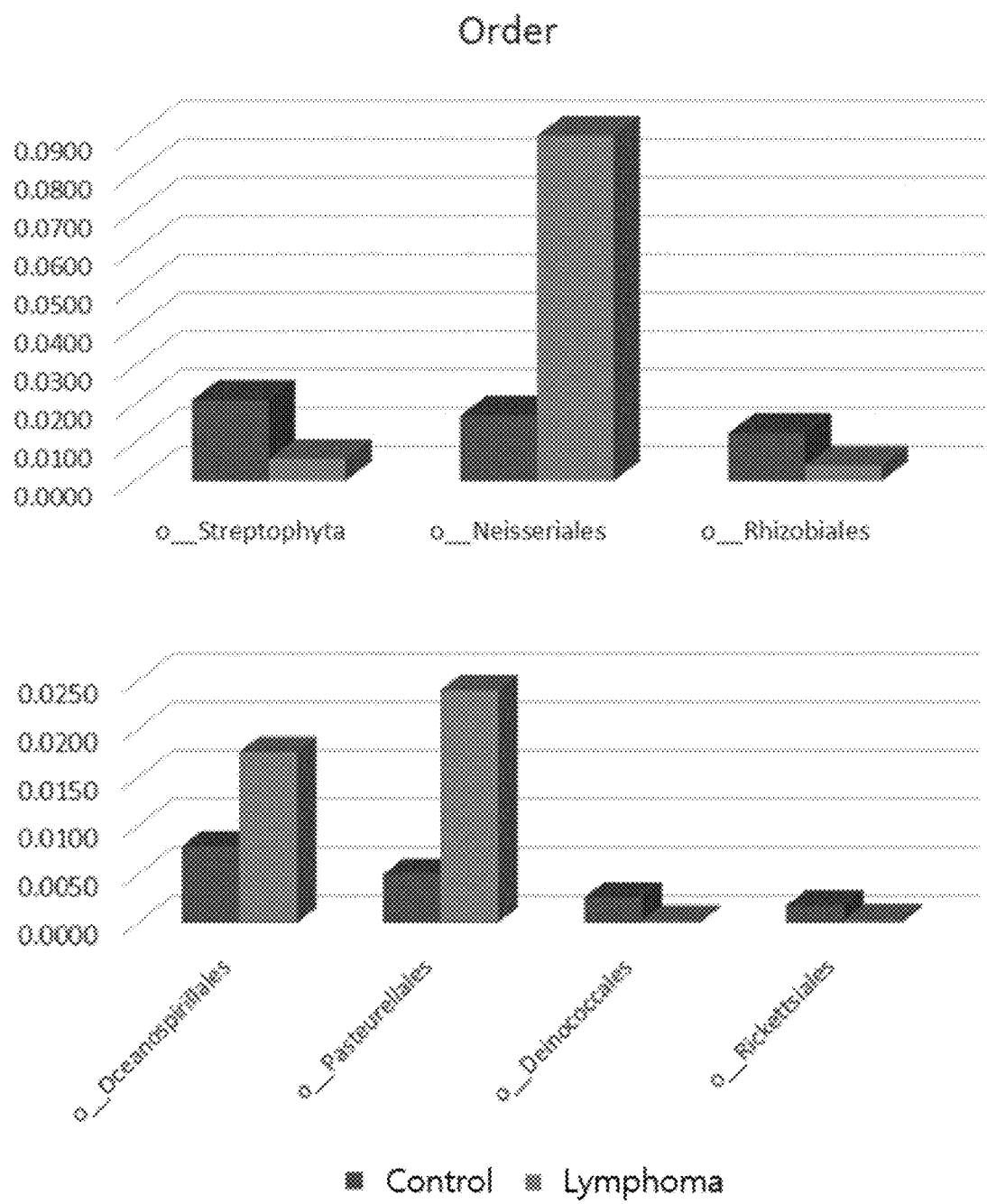
FIG. 4 is a result showing the distribution of bacteria-derived extracellular vesicles (EVs), which is significant in diagnostic performance at the order level by isolating bacteria-derived vesicles from blood of a patient with lymphoma and a normal individual, and then performing a metagenomic analysis.

As a result of analyzing bacteria-derived EVs in blood at a phylum level, a diagnostic model developed using bacteria belonging to the order Deinococcales, the order Rickettsiales, the order Streptophyta, the order Rhizobiales, the order Oceanospirillales, the order Pasteurellales, and the order Neisseriales as a biomarker exhibited significant diagnostic performance for lymphoma (see Table 4 and FIG. 4).

TABLE 4

| Taxon | Control | | Lymphoma | | t-test | | | | | |
|---|---|---|---|---|---|---|---|---|---|---|
| | Mean | SD | Mean | SD | p-value | Ratio | AUC | Accuracy | sensitivity | specificity |
| o__Deinococcales | 0.0026 | 0.0059 | 0.0002 | 0.0008 | 0.0054 | 0.09 | 0.66 | 0.65 | 0.30 | 0.94 |
| o__Rickettsiales | 0.0017 | 0.0033 | 0.0003 | 0.0014 | 0.0048 | 0.19 | 0.65 | 0.63 | 0.26 | 0.94 |
| o__Streptophyta | 0.0211 | 0.0364 | 0.0057 | 0.0142 | 0.0055 | 0.27 | 0.70 | 0.66 | 0.38 | 0.90 |
| o__Rhizobiales | 0.0125 | 0.0161 | 0.0040 | 0.0062 | 0.0007 | 0.32 | 0.73 | 0.66 | 0.45 | 0.84 |
| o__Oceanospirillales | 0.0079 | 0.0101 | 0.0176 | 0.0130 | 0.0000 | 2.24 | 0.75 | 0.68 | 0.66 | 0.70 |
| o__Pasteurellales | 0.0050 | 0.0059 | 0.0240 | 0.0245 | 0.0000 | 4.80 | 0.77 | 0.71 | 0.77 | 0.65 |
| o__Neisseriales | 0.0170 | 0.0447 | 0.0899 | 0.0486 | 0.0000 | 5.29 | 0.94 | 0.90 | 0.89 | 0.90 |

Figure 5:
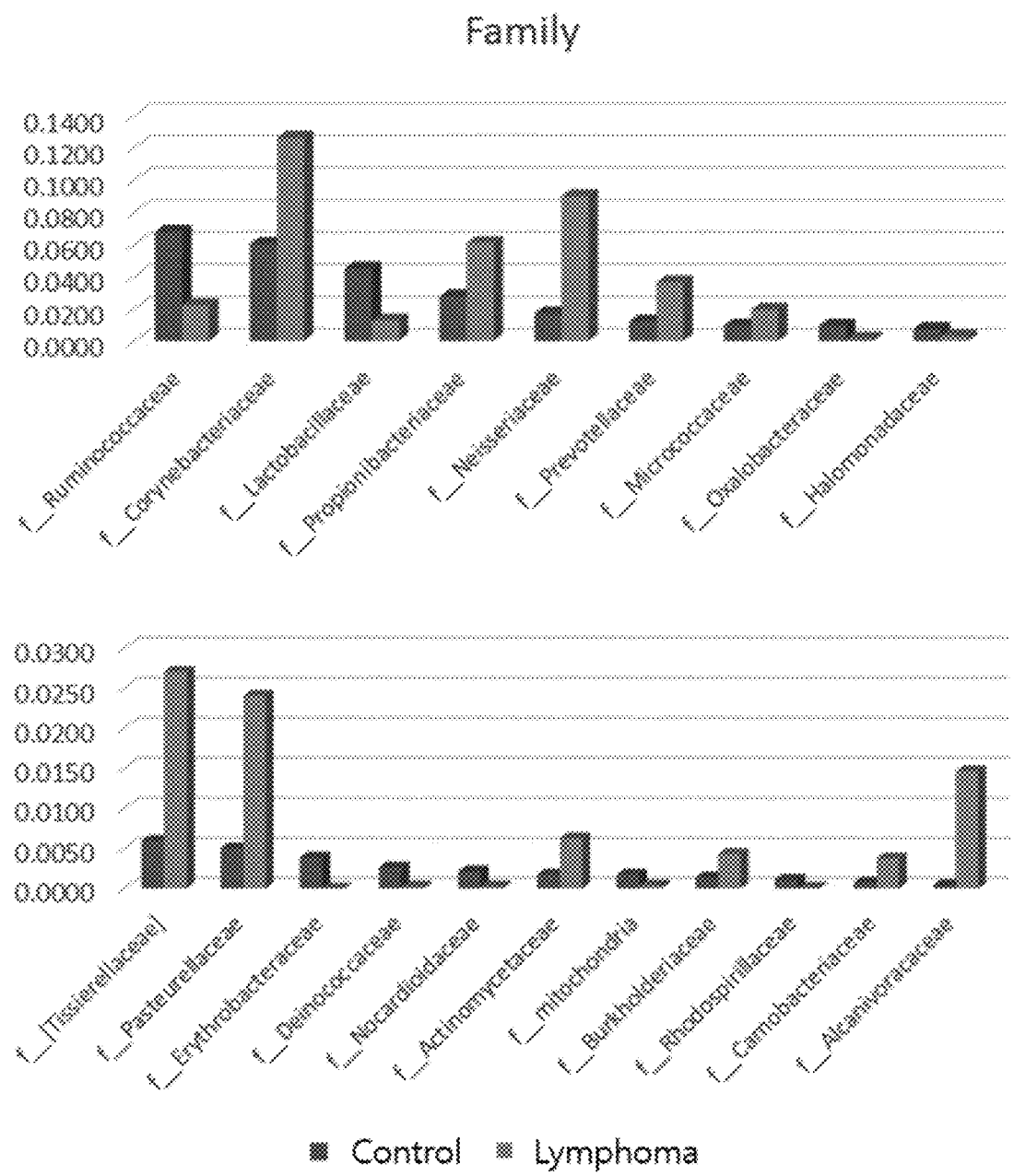
FIG. 5 is a result showing the distribution of bacteria-derived extracellular vesicles (EVs), which is significant in diagnostic performance at the family level by isolating bacteria-derived vesicles from blood of a patient with lymphoma and a normal individual, and then performing a metagenomic analysis.

As a result of analyzing bacteria-derived EVs in blood at a phylum level, a diagnostic model developed using bacteria belonging to the family Erythrobacteraceae, the family Rhodospirillaceae, the family Deinococcaceae, the family Nocardioidaceae, the family Oxalobacteraceae, the family mitochondria, the family Lactobacillaceae, the family Ruminococcaceae, the family Halomonadaceae, the family Micrococcaceae, the family Corynebacteriaceae, the family Propionibacteriaceae, the family Prevotellaceae, the family Burkholderiaceae, the family Actinomycetaceae, the family Tissierellaceae, the family Pasteurellaceae, the family Carnobacteriaceae, the family Neisseriaceae, and the family Alcanivoraceae as a biomarker exhibited significant diagnostic performance for lymphoma (see Table 5 and FIG. 5).

TABLE 5

| Taxon | Control | | Lymphoma | | t-test | | | | | |
|---|---|---|---|---|---|---|---|---|---|---|
| | Mean | SD | Mean | SD | p-value | Ratio | AUC | Accuracy | sensitivity | specificity |
| f__Erythrobacteraceae | 0.0038 | 0.0069 | 0.0000 | 0.0001 | 0.0002 | 0.00 | 0.71 | 0.71 | 0.38 | 0.98 |
| f__Rhodospirillaceae | 0.0011 | 0.0023 | 0.0001 | 0.0004 | 0.0036 | 0.07 | 0.64 | 0.64 | 0.25 | 0.97 |
| f__Deinococcaceae | 0.0026 | 0.0059 | 0.0002 | 0.0008 | 0.0056 | 0.09 | 0.66 | 0.64 | 0.28 | 0.94 |
| f__Nocardioidaceae | 0.0021 | 0.0037 | 0.0002 | 0.0012 | 0.0008 | 0.11 | 0.70 | 0.65 | 0.30 | 0.94 |
| f__Oxalobacteraceae | 0.0094 | 0.0143 | 0.0013 | 0.0022 | 0.0002 | 0.14 | 0.73 | 0.66 | 0.43 | 0.84 |
| f__mitochondria | 0.0017 | 0.0032 | 0.0003 | 0.0014 | 0.0055 | 0.19 | 0.64 | 0.63 | 0.26 | 0.94 |
| f__Lactobacillaceae | 0.0450 | 0.0527 | 0.0126 | 0.0129 | 0.0001 | 0.28 | 0.77 | 0.72 | 0.57 | 0.86 |
| f__Ruminococcaceae | 0.0678 | 0.0531 | 0.0221 | 0.0228 | 0.0000 | 0.33 | 0.78 | 0.73 | 0.55 | 0.89 |
| f__Halomonadaceae | 0.0075 | 0.0099 | 0.0030 | 0.0055 | 0.0050 | 0.40 | 0.64 | 0.67 | 0.42 | 0.89 |
| f__Micrococcaceae | 0.0095 | 0.0094 | 0.0195 | 0.0147 | 0.0000 | 2.04 | 0.73 | 0.62 | 0.62 | 0.62 |
| f__Corynebacteriaceae | 0.0602 | 0.1119 | 0.1262 | 0.0852 | 0.0007 | 2.09 | 0.81 | 0.78 | 0.74 | 0.83 |
| f__Propionibacteriaceae | 0.0276 | 0.0296 | 0.0607 | 0.0318 | 0.0000 | 2.20 | 0.82 | 0.78 | 0.79 | 0.76 |
| f__Prevotellaceae | 0.0120 | 0.0187 | 0.0363 | 0.0412 | 0.0001 | 3.02 | 0.73 | 0.67 | 0.75 | 0.60 |
| f__Burkholderiaceae | 0.0013 | 0.0026 | 0.0043 | 0.0067 | 0.0019 | 3.19 | 0.65 | 0.57 | 0.68 | 0.48 |
| f__Actinomycetaceae | 0.0017 | 0.0027 | 0.0062 | 0.0076 | 0.0000 | 3.65 | 0.71 | 0.61 | 0.68 | 0.56 |
| f__[Tissierellaceae] | 0.0059 | 0.0113 | 0.0270 | 0.0230 | 0.0000 | 4.59 | 0.85 | 0.78 | 0.79 | 0.76 |

TABLE 5-continued

| Taxon | Control Mean | SD | Lymphoma Mean | SD | t-test p-value | Ratio | AUC | Accuracy | sensitivity | specificity |
|---|---|---|---|---|---|---|---|---|---|---|
| f__Pasteurellaceae | 0.0050 | 0.0059 | 0.0240 | 0.0245 | 0.0000 | 4.81 | 0.77 | 0.71 | 0.77 | 0.65 |
| f__Carnobacteriaceae | 0.0007 | 0.0018 | 0.0037 | 0.0060 | 0.0003 | 5.12 | 0.63 | 0.61 | 0.83 | 0.43 |
| f__Neisseriaceae | 0.0170 | 0.0447 | 0.0899 | 0.0486 | 0.0000 | 5.29 | 0.94 | 0.90 | 0.89 | 0.90 |
| f__Alcanivoracaceae | 0.0004 | 0.0014 | 0.0146 | 0.0117 | 0.0000 | 39.30 | 0.93 | 0.91 | 0.94 | 0.87 |

Figure 6:
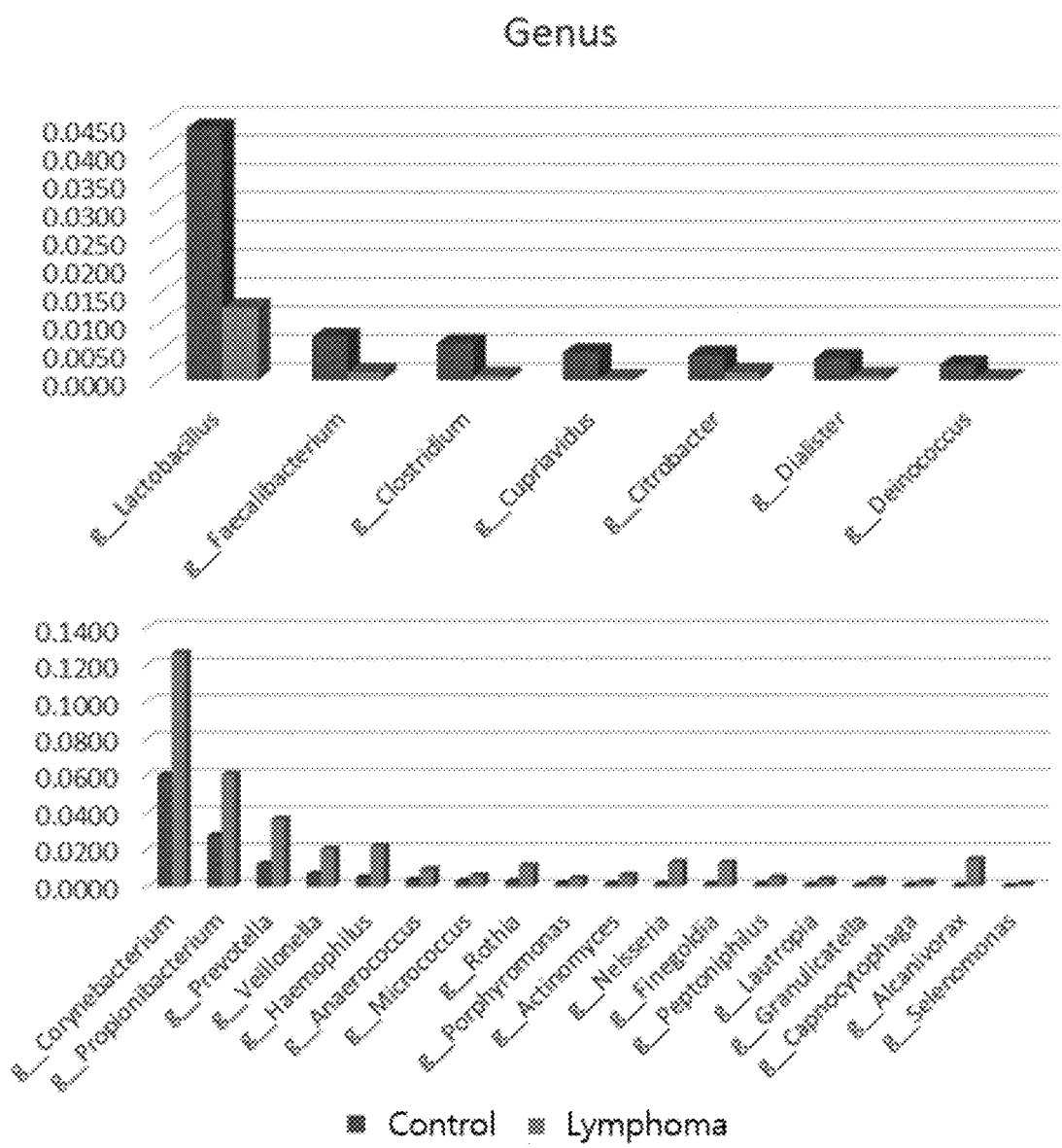
FIG. 6 is a result showing the distribution of bacteria-derived extracellular vesicles (EVs), which is significant in diagnostic performance at the genus level by isolating bacteria-derived vesicles from blood of a patient with lymphoma and a normal individual, and then performing a metagenomic analysis.

As a result of analyzing bacteria-derived EVs in blood at a phylum level, a diagnostic model developed using bacteria belonging to the genus *Cupriavidus*, the genus *Deinococcus*, the genus *Clostridium*, the genus *Dialister*, the genus *Faecalibacterium*, the genus *Lactobacillus*, the genus *Citrobacter*, the genus *Micrococcus*, the genus *Corynebacterium*, the genus *Propionibacterium*, the genus *Anaerococcus*, the genus *Porphyromonas*, the genus *Prevotella*, the genus *Veillonella*, the genus *Rothia*, the genus *Actinomyces*, the genus *Haemophilus*, the genus *Peptoniphilus*, the genus *Capnocytophaga*, the genus *Lautropia*, the genus *Granulicatella*, the genus *Finegoldia*, the genus *Neisseria*, the genus *Selenomonas*, and the genus *Alcanivorax* as a biomarker exhibited significant diagnostic performance for lymphoma (see Table 6 and FIG. 6).

TABLE 6

| Taxon | Control Mean | SD | Lymphoma Mean | SD | t-test p-value | Ratio | AUC | Accuracy | sensitivity | specificity |
|---|---|---|---|---|---|---|---|---|---|---|
| g__Cupriavidus | 0.0048 | 0.0105 | 0.0003 | 0.0011 | 0.0032 | 0.05 | 0.68 | 0.67 | 0.36 | 0.94 |
| g__Deinococcus | 0.0026 | 0.0059 | 0.0002 | 0.0008 | 0.0056 | 0.09 | 0.66 | 0.64 | 0.28 | 0.94 |
| g__Clostridium | 0.0064 | 0.0120 | 0.0007 | 0.0021 | 0.0013 | 0.11 | 0.68 | 0.66 | 0.38 | 0.90 |
| g__Dialister | 0.0037 | 0.0061 | 0.0006 | 0.0015 | 0.0007 | 0.16 | 0.68 | 0.65 | 0.38 | 0.87 |
| g__Faecalibacterium | 0.0074 | 0.0100 | 0.0014 | 0.0025 | 0.0001 | 0.18 | 0.69 | 0.70 | 0.45 | 0.90 |
| g__Lactobacillus | 0.0441 | 0.0527 | 0.0126 | 0.0129 | 0.0001 | 0.29 | 0.77 | 0.73 | 0.58 | 0.86 |
| g__Citrobacter | 0.0043 | 0.0058 | 0.0013 | 0.0033 | 0.0014 | 0.30 | 0.70 | 0.65 | 0.40 | 0.86 |
| g__Micrococcus | 0.0029 | 0.0045 | 0.0059 | 0.0049 | 0.0010 | 2.04 | 0.71 | 0.63 | 0.64 | 0.62 |
| g__Corynebacterium | 0.0602 | 0.1119 | 0.1262 | 0.0852 | 0.0007 | 2.09 | 0.81 | 0.78 | 0.74 | 0.83 |
| g__Propionibacterium | 0.0275 | 0.0295 | 0.0607 | 0.0318 | 0.0000 | 2.21 | 0.82 | 0.78 | 0.79 | 0.76 |
| g__Anaerococcus | 0.0035 | 0.0080 | 0.0092 | 0.0098 | 0.0011 | 2.60 | 0.77 | 0.75 | 0.83 | 0.68 |
| g__Porphyromonas | 0.0017 | 0.0040 | 0.0044 | 0.0063 | 0.0064 | 2.61 | 0.63 | 0.61 | 0.79 | 0.46 |
| g__Prevotella | 0.0120 | 0.0187 | 0.0363 | 0.0412 | 0.0001 | 3.02 | 0.73 | 0.67 | 0.75 | 0.60 |
| g__Veillonella | 0.0066 | 0.0145 | 0.0202 | 0.0214 | 0.0001 | 3.07 | 0.78 | 0.73 | 0.81 | 0.67 |
| g__Rothia | 0.0028 | 0.0040 | 0.0113 | 0.0122 | 0.0000 | 4.08 | 0.73 | 0.70 | 0.79 | 0.62 |
| g__Actinomyces | 0.0013 | 0.0023 | 0.0061 | 0.0076 | 0.0000 | 4.58 | 0.72 | 0.65 | 0.74 | 0.57 |
| g__Haemophilus | 0.0047 | 0.0059 | 0.0219 | 0.0232 | 0.0000 | 4.68 | 0.77 | 0.72 | 0.79 | 0.67 |
| g__Peptoniphilus | 0.0010 | 0.0034 | 0.0048 | 0.0093 | 0.0040 | 4.75 | 0.70 | 0.67 | 0.85 | 0.52 |
| g__Capnocytophaga | 0.0005 | 0.0014 | 0.0022 | 0.0039 | 0.0015 | 4.81 | 0.61 | 0.55 | 0.81 | 0.33 |
| g__Lautropia | 0.0007 | 0.0020 | 0.0037 | 0.0059 | 0.0005 | 4.94 | 0.67 | 0.62 | 0.81 | 0.46 |
| g__Granulicatella | 0.0007 | 0.0018 | 0.0037 | 0.0059 | 0.0003 | 5.36 | 0.64 | 0.62 | 0.83 | 0.44 |
| g__Finegoldia | 0.0012 | 0.0026 | 0.0128 | 0.0178 | 0.0000 | 10.61 | 0.83 | 0.76 | 0.85 | 0.68 |
| g__Neisseria | 0.0012 | 0.0019 | 0.0130 | 0.0141 | 0.0000 | 10.79 | 0.79 | 0.75 | 0.85 | 0.67 |
| g__Selenomonas | 0.0001 | 0.0005 | 0.0012 | 0.0032 | 0.0066 | 13.94 | 0.66 | 0.59 | 0.55 | 0.62 |
| g__Alcanivorax | 0.0004 | 0.0014 | 0.0146 | 0.0117 | 0.0000 | 39.30 | 0.93 | 0.91 | 0.94 | 0.87 |

The above description of the present invention is provided only for illustrative purposes, and it will be understood by one of ordinary skill in the art to which the present invention pertains that the invention may be embodied in various modified forms without departing from the spirit or essential characteristics thereof. Thus, the embodiments described herein should be considered in an illustrative sense only and not for the purpose of limitation.

INDUSTRIAL APPLICABILITY

The method of providing information for diagnosing lymphoma through a bacterial metagenomic analysis according to the present invention may be used for predicting the risk of lymphoma onset and diagnosing lymphoma by performing a bacterial metagenomic analysis using normal individual-derived and subject-derived samples to analyze an increase or decrease in the content of specific bacteria-derived extracellular vesicles.

The invention claimed is:

1. A method of providing information for diagnosing lymphoma, the method comprising:
    (a) isolating bacteria-derived extracellular vesicles from blood samples obtained from a subject who is suspected of being at risk of developing lymphoma and from a normal individual;
    (b) extracting DNAs from the bacteria-derived extracellular vesicles isolated from the samples;
    (c) detecting the content of extracellular vesicles in the samples by performing polymerase chain reaction (PCR) on the extracted DNA using a pair of primers comprising SEQ ID NO: 1 and SEQ ID NO: 2, and then performing metagenomic sequencing the product of the PCR to determine content of bacteria-derived extracellular vesicles in each sample;
    (d) selecting strains exhibiting a p-value less than 0.05 between the two groups in a t-test and a mean value difference of two-fold or more between two groups; and
    (e) forming a diagnostic model for lymphoma consisting of the extracellular vesicles derived from: (i) the genus *Cupriavidus*, the genus *Deinococcus*, the genus *Clostridium*, the genus *Dialister*, the genus *Faecalibacterium*, the genus *Lactobacillus*, and the genus *Citrobacter*, and (ii) the genus *Micrococcus*, the genus *Corynebacterium*, the genus *Propionibacterium*, the genus *Anaerococcus*, the genus *Porphyromonas*, the genus *Prevotella*, the genus *Veillonella*, the genus *Rothia*, the genus *Actinomyces*, the genus *Haemophilus*, the genus *Peptoniphilus*, the genus *Capnocytophaga*, the genus *Lautropia*, the genus *Granulicatella*, the genus *Finegoldia*, the genus *Neisseria*, the genus *Selenomonas*, and the genus *Alcanivorax* wherein in the diagnostic model, an increase in the content of the extracellular vesicles derived from the 18 genera in (ii) by two-fold or more and a decrease in the content of the extracellular vesicles derived from the 7 genera in (i) by two-fold or more in the sample from the subject, in comparison with the content of extracellular vesicles in the sample from the normal individual indicate a risk of developing lymphoma.

2. A method of providing information for diagnosing lymphoma, the method comprising:
    (a) isolating bacteria-derived extracellular vesicles from a blood sample obtained from a subject who is suspected of being at risk of developing lymphoma and from a normal individual group;
    (b) extracting DNAs from the bacteria-derived extracellular vesicles isolated from the samples;
    (c) detecting the content of extracellular vesicles in the samples by performing polymerase chain reaction (PCR) on the extracted DNA using a pair of primers comprising SEQ ID NO: 1 and SEQ ID NO: 2, and then performing metagenomic sequencing of the product of the PCR to determine content of bacteria-derived extracellular vesicles in each sample;
    (d) selecting strains exhibiting a p-value less than 0.05 between the two groups in a t-test and a mean value difference of two-fold or more between two groups; and
    (e) forming a diagnostic model for lymphoma consisting of the extracellular vesicles derived from the genus *Finegoldia*, the genus *Alcanivorax*, the genus *Corynebacterium*, and the genus *Propionibacterium*, wherein Area Under the Curve (AUC) value of the four extracellular vesicles is 0.81 or higher, calculated by logistic regression analysis, and wherein the increase of the content of the four extracellular vesicles by two-fold or more, in comparison with the content of the extracellular vesicles in the sample from the normal individual, indicate a risk of developing lymphoma.

* * * * *